United States Patent
Karim et al.

(10) Patent No.: US 10,239,800 B2
(45) Date of Patent: *Mar. 26, 2019

(54) CATALYST AND PROCESS FOR SELECTIVE PRODUCTION OF LOWER HYDROCARBONS C1—C5 FROM SYNGAS WITH LOW METHANE AND $CO_2$ PRODUCTION

(71) Applicant: SAUDI BASIC INDUSTRIES CORPORATION, Riyadh (SA)

(72) Inventors: Khalid Karim, Riyadh (SA); Mohammed Al-Semahi, Riyadh (SA); Asad Khan, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/372,948

(22) Filed: Dec. 8, 2016

(65) Prior Publication Data

US 2017/0217851 A1      Aug. 3, 2017

Related U.S. Application Data

(63) Continuation of application No. 14/409,017, filed as application No. PCT/EP2013/063311 on Jun. 25, 2013, now Pat. No. 9,545,620.

(Continued)

(51) Int. Cl.
*B01J 23/75* (2006.01)
*C07C 1/04* (2006.01)

(Continued)

(52) U.S. Cl.
CPC ............... *C07C 1/044* (2013.01); *B01J 21/08* (2013.01); *B01J 23/8892* (2013.01);
(Continued)

(58) Field of Classification Search
None
See application file for complete search history.

(56) References Cited

U.S. PATENT DOCUMENTS 3,932,552 A    1/1976  Starks
4,131,568 A   12/1978  Bartish
(Continued)

FOREIGN PATENT DOCUMENTS

CN     1187180 A     7/1998
CN   101679140 A     3/2010
(Continued)

OTHER PUBLICATIONS

Evonik ("The history of Aerosil®", pp. 1-2) (Year: 1941).*
(Continued)

*Primary Examiner* — Medhanit W Bahta
(74) *Attorney, Agent, or Firm* — Ballard Spahr LLP

(57) ABSTRACT

A catalyst composition containing cobalt manganese oxide which is modified with silicon in the form of a hydrophilic silica, the catalyst also containing at least one of lanthanum, phosphorus, Fe, Zr, and Zn, and optionally one or more basic elements selected from the group of alkali metal, alkaline earth metal, and transition metals. Also, methods for preparing and using the catalyst composition for producing aliphatic and aromatic hydrocarbons using the catalyst composition.

15 Claims, 2 Drawing Sheets

Related U.S. Application Data

(60) Provisional application No. 61/665,005, filed on Jun. 27, 2012.

(51) Int. Cl.

| | | |
|---|---|---|
| *B01J 21/08* | (2006.01) | |
| *C07C 1/06* | (2006.01) | |
| *C07C 5/327* | (2006.01) | |
| *C07C 4/00* | (2006.01) | |
| *B01J 27/187* | (2006.01) | |
| *B01J 37/08* | (2006.01) | |
| *B01J 37/16* | (2006.01) | |
| *B01J 37/06* | (2006.01) | |
| *B01J 37/04* | (2006.01) | |
| *B01J 37/03* | (2006.01) | |
| *B01J 23/889* | (2006.01) | |
| *C07C 4/06* | (2006.01) | |
| *C07C 5/32* | (2006.01) | |
| *B01J 37/18* | (2006.01) | |
| *B01J 23/80* | (2006.01) | |
| *B01J 23/84* | (2006.01) | |
| *B01J 27/185* | (2006.01) | |
| *B01J 23/32* | (2006.01) | |

(52) U.S. Cl.
CPC ........... *B01J 27/187* (2013.01); *B01J 37/031* (2013.01); *B01J 37/04* (2013.01); *B01J 37/06* (2013.01); *B01J 37/08* (2013.01); *B01J 37/16* (2013.01); *B01J 37/18* (2013.01); *C07C 1/0435* (2013.01); *C07C 1/0485* (2013.01); *C07C 1/06* (2013.01); *C07C 4/00* (2013.01); *C07C 4/06* (2013.01); *C07C 5/32* (2013.01); *C07C 5/327* (2013.01); *B01J 23/32* (2013.01); *B01J 23/80* (2013.01); *B01J 23/84* (2013.01); *B01J 27/1853* (2013.01); *B01J 2523/3706* (2013.01); *C07C 2521/06* (2013.01); *C07C 2521/08* (2013.01); *C07C 2523/06* (2013.01); *C07C 2523/10* (2013.01); *C07C 2523/34* (2013.01); *C07C 2523/745* (2013.01); *C07C 2523/75* (2013.01); *C07C 2523/889* (2013.01); *C07C 2527/14* (2013.01); *C07C 2527/187* (2013.01); *Y02P 20/52* (2015.11)

(56) References Cited

U.S. PATENT DOCUMENTS

| | | |
|---|---|---|
| 4,177,203 A | 12/1979 | Kolbel et al. |
| 4,451,579 A | 5/1984 | Lemanski et al. |
| 5,248,701 A | 9/1993 | Soled et al. |
| 5,958,608 A | 9/1999 | Jahn |
| 5,958,985 A | 9/1999 | Geerlings et al. |
| 5,981,608 A | 11/1999 | Geerlings et al. |
| 5,990,369 A | 11/1999 | Barger et al. |
| 6,586,649 B1 | 7/2003 | Botha et al. |
| 7,253,136 B2 | 8/2007 | Mauldin et al. |
| 7,365,040 B2 | 4/2008 | Van Berge et al. |
| 7,375,055 B2 | 5/2008 | Van Berge et al. |
| 8,153,851 B2 | 4/2012 | Gartside et al. |
| 9,416,067 B2 | 8/2016 | Karim et al. |
| 9,422,204 B2 | 8/2016 | Karim et al. |
| 9,545,620 B2 | 1/2017 | Karim et al. |
| 2001/0006984 A1 | 7/2001 | Lapidus et al. |
| 2002/0010221 A1 | 1/2002 | Ionkina et al. |
| 2003/0027874 A1 | 2/2003 | Herron et al. |
| 2005/0113463 A1 | 5/2005 | O'Rear et al. |
| 2008/0033218 A1 | 2/2008 | Lattner et al. |
| 2008/0262114 A1 | 10/2008 | Reynhout |
| 2010/0069589 A1 | 3/2010 | Bradin |
| 2012/0083539 A1 | 4/2012 | Fu et al. |
| 2012/0115967 A1* | 5/2012 | Bezemer .................. B01J 21/08 518/728 |

FOREIGN PATENT DOCUMENTS

| | | |
|---|---|---|
| CN | 101745403 A | 6/2010 |
| CN | 102500425 A * | 6/2012 |
| EA | 024093 B1 | 8/2016 |
| EP | 1970361 A1 | 9/2008 |
| EP | 2422876 A1 | 2/2012 |
| EP | 2439185 A1 | 4/2012 |
| JP | S 59179154 A | 10/1984 |
| JP | 2007-512328 A | 5/2007 |
| WO | WO-0176736 A1 | 10/2001 |
| WO | WO-2003/041860 A2 | 5/2003 |
| WO | WO-2003/076074 A1 | 9/2003 |
| WO | WO-2005/054163 A1 | 6/2005 |
| WO | WO-2008147836 A1 | 12/2008 |
| WO | WO-2012/084160 A1 | 6/2012 |
| WO | WO-2014/001350 A1 | 1/2014 |
| WO | WO-2014/001354 A1 | 1/2014 |

OTHER PUBLICATIONS

Colley, S., et al., Carbon Monoxide Hydrogenation Using Cobalt Manganese Oxide Catalysts: Initial Catalyst Optimization Studies (1988) Ind. Eng. Chem. Res. 27:1339-1344.

Commereuc, D., et al., "Catalytic synthesis of low molecular weight olefins from CO and H2 with Fe(CO)5, Fe3(CO)12, and [HFe3(CO)11]—supported on inorganic oxides" (1980) J. Chem. Soc., Chem. Commun. 154-155.

Dry (2004) Stud. Surf. Sci. Catal 152:197-230 in "Fischer-Tropsch technology" eds. Steynberg and Dry.

Keyser, M J et al., "Fischer-Tropsch studies with cobalt-manganese oxide catalysts: Synthesis performance in a fixed bed reactor" Applied Catalysis A: General. 171(1):99-107.(1998).

Liu Xijing et al., Effect of isomorphic substitution of lanthanum on mesoporous silica as support for Co Fisher-Tropsch synthesis catalysts, Journal of Guizhou University, (Natural Science), vol. 27, No. 3, pp. 25-27 (2010).

Mirzaei, et al.; "Fischer-Tropsch Synthesis Over Iron Manganese Catalysts: Effect of Preparation and Operating Conditions on Catalyst Performance" Advances in Physical Chemistry; vol. 2009; Article ID: 151489; (12 Pages).

Okuhara, T., et al., "Synthesis of light olefins from CO and H2 over highly dispersed Ru/K—Al2O3 derived from Ru3(CO)12" (1981) J. Chem. Soc., Chem. Commun. 1114-1115.

Van Der Riet, M., et al., "Selective formation of C3 hydrocarbons from co + H2 using cobalt—manganese oxide catalysts" (1986) J. Chem. Soc. Chem. Commun 798-799.

International Search Report and Written Opinion were dated Jan. 31, 2012 by the International Searching Authority for International Application No. PCT/EP2011/006374, which was filed on Dec. 15, 2011 and published as WO 2012/084160 A1 on Jun. 28, 2012 (Applicant—Sabic BAsic Industries Corporation) (10 pages).

International Preliminary Report on Patentability was dated Jun. 25, 2013 by the International Searching Authority for International Application No. PCT/EP2011/006374, which was filed on Dec. 15, 2011 and published as WO 2012/084160 A1 on Jun. 28, 2012 (Applicant—Sabic Basic Industries Corporation) (7 pages).

International Search Report and Written Opinion were dated Oct. 10, 2013 by the International Searching Authority for International Application No. PCT/EP2013/063311, which was filed on Jun. 25, 2013 and published as WO/2014/001354 on Jan. 3, 2014 (Applicant—Sabic Basic Industries Corporation) (8 pages).

International Preliminary Report on Patentability was dated Dec. 31, 2014 by the International Searching Authority for International Application No. PCT/EP2013/063311, which was filed on Jun. 25, 2013 and published as WO/2014/001354 on Jan. 3, 2014 (Applicant—Sabic Basic Industries Corporation) (3 pages).

(56) References Cited

OTHER PUBLICATIONS

International Search Report and Written Opinion were dated Oct. 2, 2013 by the International Searching Authority for International Application No. PCT/EP2013/063307, which was filed on Jun. 25, 2013 and published as WO/2014/001350 on Jan. 3, 2014 (Applicant—Sabic Basic Industries Corporation) (10 pages).
International Preliminary Report on Patentability was dated Dec. 31, 2014 by the International Searching Authority for International Application No. PCT/EP2013/063307, which was filed on Jun. 25, 2013 and published as WO/2014/001350 on Jan. 3, 2014 (Applicant—Sabic Basic Industries Corporation) (8 pages).
First Office Action was dated May 21, 2014 by the SIPO for CN Application No. 201180065826.0, which was filed on Dec. 15, 2011 and published as CN103339230A on Oct. 2, 2013 (Applicant—Sabic Basic Industries Corporation) (Original—5 pages// Translated—7 pages).
Notification to Grant Patent Right for Invention was dated Dec. 31, 2014 by the SIPO for CN Application No. 201180065826.0, which was filed on Dec. 15, 2011 and published as CN103339230A on Oct. 2, 2013 (Applicant—Sabic Basic Industries Corporation) (Original—1 page// Translated—2 pages).
First Office Action was dated Apr. 23, 2015 by the Eurasian Patent Office for EA Application No. 201300736, which was filed on Dec. 15, 2011 and granted as EA 024093 on Aug. 31, 2016 (Applicant—Sabic Basic Industries Corporation) (Original—1 page // Translated—1 page).
Second Office Action was dated Oct. 2, 2015 by the Eurasian Patent Office for EA Application No. 201300736, which was filed on Dec. 15, 2011 and granted as EA 024093 on Aug. 31, 2016 (Applicant—Sabic Basic Industries Corporation) (Original—1 page // Translated—1 page).
Third Office Action was dated Dec. 30, 2015 by the Eurasian Patent Office for EA Application No. 201300736, which was filed on Dec. 15, 2011 and granted as EA 024093 on Aug. 31, 2016 (Applicant—Sabic Basic Industries Corporation) (Original—1 page // Translated—1 page).
Certificate of Patent was issued on Aug. 31, 2016 by the Eurasian Patent Office for EA Application No. 201300736, which was filed on Dec. 15, 2011 and granted as EA 024093 on Aug. 31, 2016 (Applicant—Sabic Basic Industries Corporation) (Original—1 page // Translated—1 page).
First Examination Report was dated Oct. 3, 2016 by the Patent Office of the Cooperation Council for the Arab States of the Gulf for GC Application No. GC 2011-20076, which was filed on Dec. 20, 2011 and granted as GC 0006185 on Oct. 1, 2017 (Applicant—Saudi Basic Industries Corporation) (6 pages).
Second Examination Report was dated Oct. 25, 2016 by the Patent Office of the Cooperation Council for the Arab States of the Gulf for GC Application No. GC 2011-20076, which was filed on Dec. 20, 2011 and granted as GC 0006185 on Oct. 1, 2017 (Applicant—Saudi Basic Industries Corporation) (4 pages).
Third Examination Report was dated Feb. 19, 2017 by the Patent Office of the Cooperation Council for the Arab States of the Gulf for GC Application No. GC 2011-20076, which was filed on Dec. 20, 2011 and granted as GC 0006185 on Oct. 1, 2017 (Applicant—Saudi Basic Industries Corporation) (4 pages).
Grant of Patent was issued on Oct. 1, 2017 by the Patent Office of the Cooperation Council for the Arab States of the Gulf for GC Application No. GC2011-20076, which was filed on Dec. 20, 2011 and granted as GC 0006185 on Oct. 1, 2017 (Applicant—Saudi Basic Industries Corporation) (1 page).
Notification of Reasons for Refusal was dated Jun. 2, 2015 by the Japanese Patent Office for JP Application No. 2013-545093, which was filed on Dec. 15, 2011 and granted as JP2013545093 on Oct. 23, 2015 (Applicant—Saudi Basic Industries Corporation) (Original—4 page// Translated—3 pages).
Decision to Grant a Patent was dated Sep. 15, 2015 by the Japanese Patent Office for JP Application No. 2013-545093, which was filed on Dec. 15, 2011 and granted as JP2013545093 on Oct. 23, 2015 (Applicant—Saudi Basic Industries Corporation) (Original—4 page// Translated—3 pages).
Requirement for Restriction/Election was dated Sep. 9, 2014 by the USPTO for U.S. Appl. No. 13/995,646, filed Jun. 19, 2013 and now U.S. Pat. No. 9,416,067 on Aug. 16, 2016 (Inventor—Khalid Karim, et al.) (8 pages).
Response to Requirement for Restriction/Election was dated Nov. 14, 2014 to the USPTO for U.S. Appl. No. 13/995,646, filed Jun. 19, 2013 and now U.S. Pat. No. 9,416,067 on Aug. 16, 2016 (Inventor—Khalid Karim, et al.) (9 pages).
Non Final Rejection was dated Jan. 2, 2015 by the USPTO for U.S. Appl. No. 13/995,646, filed Jun. 19, 2013 and now U.S. Pat. No. 9,416,067 on Aug. 16, 2016 (Inventor—Khalid Karim, et al.) (9 pages).
Response to Non Final Rejection was dated Apr. 2, 2015 to the USPTO for U.S. Appl. No. 13/995,646, filed Jun. 19, 2013 and now U.S. Pat. No. 9,416,067 on Aug. 16, 2016 (Inventor—Khalid Karim, et al.) (14 pages).
Final Rejection was dated Jul. 16, 2015 by the USPTO for U.S. Appl. No. 13/995,646, filed Jun. 19, 2013 and now U.S. Pat. No. 9,416,067 on Aug. 16, 2016 (Inventor—Khalid Karim, et al.) (12 pages).
Response to Final Rejection was dated Aug. 31, 2015 to the USPTO for U.S. Appl. No. 13/995,646, filed Jun. 19, 2013 and now U.S. Pat. No. 9,416,067 on Aug. 16, 2016 (Inventor—Khalid Karim, et al.) (12 pages).
Notice of Allowance was dated May 6, 2016 by the USPTO for U.S. Appl. No. 13/995,646, filed Jun. 19, 2013 and now U.S. Pat. No. 9,416,067 on Aug. 16, 2016 (Inventor—Khalid Karim, et al.) (8 pages).
Amendment after Notice of Allowance (Rule 312) was dated Jun. 23, 2016 to the USPTO for U.S. Appl. No. 13/995,646, filed Jun. 19, 2013 and now U.S. Pat. No. 9,416,067 on Aug. 16, 2016 (Inventor—Khalid Karim, et al.) (2 pages).
Notice of Allowance was dated Jun. 27, 2016 by the USPTO for U.S. Appl. No. 13/995,646, filed Jun. 19, 2013 and now U.S. Pat. No. 9,416,067 on Aug. 16, 2016 (Inventor—Khalid Karim, et al.) (2 pages).
Issue Notification was dated Jul. 27, 2016 by the USPTO for U.S. Appl. No. 13/995,646, filed Jun. 19, 2013 and now U.S. Pat. No. 9,416,067 on Aug. 16, 2016 (Inventor—Khalid Karim, et al.) (1 page).
First Office Action was dated Dec. 10, 2015 by the SIPO for CN Application No. 201380032020.0 which was filed on Jun. 25, 2013 and published as CN 104602816A on May 6, 2015 (Applicant—Sabic Basic Industries Corporation)(Original—8 pages// Translated—11 pages).
Second Office Action was dated Aug. 31, 2016 by the SIPO for CN Application No. 201380032020.0 which was filed on Jun. 25, 2013 and published as CN 104602816A on May 6, 2015 (Applicant—Sabic Basic Industries Corporation) (Original—8 pages// Translated—12 pages).
Third Office Action was dated Jan. 20, 2017 by the SIPO for CN Application No. 201380032020.0 which was filed on Jun. 25, 2013 and published as CN 104602816A on May 6, 2015 (Applicant—Sabic Basic Industries Corporation) (Original—8 pages// Translated—13 pages).
Fourth Office Action was dated Oct. 16, 2017 by the SIPO for CN Application No. 201380032020.0 which was filed on Jun. 25, 2013 and published as CN 104602816A on May 6, 2015 (Applicant—Sabic Basic Industries Corporation) (Original—8 pages// Translated—9 pages).
First Office Action was dated Mar. 19, 2015 by the Eurasian Patent Office for EA Application No. 201590105, which was filed on Jun. 25, 2013 (Applicant—Sabic Basic Industries Corporation) (Original—3 pages // Translated—5 pages).
Examination Report was dated Oct. 25, 2017 by the Patent Office of the Cooperation Council for the Arab States of the Gulf for GC Application No. GC 2013-24762, which was filed on Jun. 25, 2013 (Applicant—Saudi Basic Industries Corporation) (3 pages).

(56) References Cited

OTHER PUBLICATIONS

Preliminary Amendment was dated Dec. 18, 2014 to the USPTO for U.S. Appl. No. 14/409,017, filed Dec. 18, 2014 and now U.S. Pat. No. 9,545,620 on Jan. 17, 2017 (Inventor—Khalid Karim et al.) (11 pages).

Requirement for Restriction/Election was dated Dec. 3, 2015 by the USPTO for U.S. Appl. No. 14/409,017, filed Dec. 18, 2014 and now U.S. Pat. No. 9,545,620 on Jan. 17, 2017 (Inventor—Khalid Karim et al.) (6 pages).

Response to Requirement for Restriction/Election was dated Feb. 3, 2016 tp the USPTO for U.S. Appl. No. 14/409,017, filed Dec. 18, 2014 and now U.S. Pat. No. 9,545,620 on Jan. 17, 2017 (Inventor—Khalid Karim et al.) (10 pages).

Non Final Rejection was dated Apr. 4, 2016 by the USPTO for U.S. Appl. No. 14/409,017, filed Dec. 18, 2014 and now U.S. Pat. No. 9,545,620 on Jan. 17, 2017 (Inventor—Khalid Karim et al.) (10 pages).

Response to Non Final Rejection was dated Jul. 5, 2016 to the USPTO for U.S. Appl. No. 14/409,017, filed Dec. 18, 2014 and now U.S. Pat. No. 9,545,620 on Jan. 17, 2017 (Inventor—Khalid Karim et al.) (12 pages).

Notice of Allowance was dated Sep. 9, 2016 by the USPTO for U.S. Appl. No. 14/409,017, filed Dec. 18, 2014 and now U.S. Pat. No. 9,545,620 on Jan. 17, 2017 (Inventor—Khalid Karim et al.) (14 pages).

Issue Notification was dated Dec. 28, 2016 by the USPTO for U.S. Appl. No. 14/409,017, filed Dec. 18, 2014 and now U.S. Pat. No. 9,545,620 on Jan. 17, 2017 (Inventor—Khalid Karim et al.) (1 page).

First Office Action was dated Nov. 30, 2015 by the SIPO for CN Application No. 201380032021.5, which was filed on Jun. 25, 2013 and published as CN104379542A on Feb. 25, 2015 (Applicant—Sabic Basic Industries Corporation) (Original—5 pages// Translated—7 pages).

Second Office Action was dated Oct. 8, 2016 by the SIPO for CN Application No. 201380032021.5, which was filed on Jun. 25, 2013 and published as CN104379542A on Feb. 25, 2015 (Applicant—Sabic Basic Industries Corporation) (Original—6 pages// Translated—10 pages).

Third Office Action was dated Apr. 24, 2017 by the SIPO for CN Application No. 201380032021.5, which was filed on Jun. 25, 2013 and published as CN104379542A on Feb. 25, 2015 (Applicant—Sabic Basic Industries Corporation) (Original—6 pages// Translated—6 pages).

Notification to Grant Patent Right for Invention was dated Nov. 6, 2017 by the SIPO for CN Application No. 201380032021.5, which was filed on Jun. 25, 2013 and published as CN104379542A on Feb. 25, 2015 (Applicant—Sabic Basic Industries Corporation) (Original—6 pages// Translated—2 pages).

Communication pursuant to Article 94(3) EPC was dated Sep. 14, 2017 by the European Patent Office for EP Application No. 13734700.1 which was filed on Jun. 25, 2013 and published as EP 2864276 on Apr. 29, 2015 (Applicant—Sabic Basic Industries Corporation) (8 pages).

First Examination Report was dated Apr. 19, 2016 by the Patent Office of the Cooperation Council for the Arab States of the Gulf for GC Application No. GC 2013-24763, which was filed on Jun. 25, 2013 and granted as GC0005326 on Apr. 9, 2017 (Applicant—Saudi Basic Industries Corporation) (3 pages).

Second Examination Report was dated Aug. 29, 2016 by the Patent Office of the Cooperation Council for the Arab States of the Gulf for GC Application No. GC 2013-24763, which was filed on Jun. 25, 2013 and granted as GC0005326 on Apr. 9, 2017 (Applicant—Saudi Basic Industries Corporation) (3 pages).

Letters patent issued on Apr. 9, 2017 by the Patent Office of the Cooperation Council for the Arab States of the Gulf for GC Application No. GC 2013-24763, which was filed on Jun. 25, 2013 and granted as GC0005326 on Apr. 9, 2017 (Applicant—Saudi Basic Industries Corporation) (Original—29 pages// Translated—3 pages).

Preliminary Amendment was dated Sep. 18, 2013 to the USPTO for U.S. Appl. No. 14/005,973, filed Sep. 18, 2013 and now U.S. Pat. No. 9,422,204 on Aug. 23, 2016 (Inventor—Khalid Karim et al.) (32 pages).

Preliminary Amendment was dated Mar. 31, 2014 to the USPTO for U.S. Appl. No. 14/005,973, filed Sep. 18, 2013 and now U.S. Pat. No. 9,422,204 on Aug. 23, 2016 (Inventor—Khalid Karim et al.) (5 pages).

Non Final Rejection was dated Aug. 13, 2015 by the USPTO for U.S. Appl. No. 14/005,973, filed Sep. 18, 2013 and now U.S. Pat. No. 9,422,204 on Aug. 23, 2016 (Inventor—Khalid Karim et al.) (9 pages).

Response to Non Final Rejection was dated Jan. 13, 2016 to the USPTO for U.S. Appl. No. 14/005,973, filed Sep. 18, 2013 and now U.S. Pat. No. 9,422,204 on Aug. 23, 2016 (Inventor—Khalid Karim et al.) (8 pages).

Notice of Allowance was dated Apr. 14, 2016 by the USPTO for U.S. Appl. No. 14/005,973, filed Sep. 18, 2013 and now U.S. Pat. No. 9,422,204 on Aug. 23, 2016 (Inventor—Khalid Karim et al.) (8 pages).

Notice of Allowance was dated Jun. 16, 2016 by the USPTO for U.S. Appl. No. 14/005,973, filed Sep. 18, 2013 and now U.S. Pat. No. 9,422,204 on Aug. 23, 2016 (Inventor—Khalid Karim et al.) (2 pages).

Issue Notification was dated Aug. 3, 2016 by the USPTO for U.S. Appl. No. 14/005,973, filed Sep. 18, 2013 and now U.S. Pat. No. 9,422,204 on Aug. 23, 2016 (Inventor—Khalid Karim et al.) (1 page).

* cited by examiner

CATALYST AND PROCESS FOR SELECTIVE PRODUCTION OF LOWER HYDROCARBONS C1—C5 FROM SYNGAS WITH LOW METHANE AND CO₂ PRODUCTION

CROSS-REFERENCE TO RELATED APPLICATIONS

The present application is a continuation of and claims the benefit of priority to U.S. Application No. 14/409,017, filed Dec. 18, 2014, which is a U.S. National Phase Application of International Application No. PCT/EP2013/063311, filed Jun. 25, 2013, which claims priority to U.S. Application No. 61/665,005, filed Jun. 27, 2012, all of which applications are incorporated herein fully by this reference.

BACKGROUND

Gaseous mixtures comprising hydrogen ($H_2$) and carbon monoxide (CO) can be converted into a hydrocarbon product stream by a catalytic process known as Fischer-Tropsch synthesis (F-T synthesis). The most common catalysts useful in F-T synthesis ("F-T catalysts") are based on Fe and/or Co, although Ni- and Ru-based catalysts have also been described (see e.g. U.S. Pat. No. 4,177,203; Commereuc (1980) J. Chem. Soc., Chem. Commun. 154-155; Okuhara (1981) J. Chem. Soc., Chem. Commun. 1114-1115). Generally, Ni-based catalysts are relatively more selective for producing methane whereas Co-, Fe- and Ru-based catalysts are more selective for hydrocarbons having at least two carbon atoms ($C_{2+}$ hydrocarbons). Moreover, the selectivity for $C_{2+}$ hydrocarbons can be increased by decreasing the $H_2$:CO ratio, decreasing the reaction temperature and decreasing the reactor pressure.

It has been previously described that unsupported cobalt-manganese oxide catalysts can be used as an F-T catalyst having an improved selectivity for $C_3$ hydrocarbons and a suppressed $CH_4$ selectivity (see Van der Riet (1986) J. Chem. Soc. Chem. Commun 798-799 and Keyser (1998) Applied Catalysis 171:99-107). The unsupported cobalt-manganese oxide composition suitable for use as F-T catalyst was produced by a process comprising the steps of co-precipitating cobalt and manganese oxides from cobalt- and manganese-comprising solution, calcining the precipitate to form a calcined catalyst precursor and reducing the calcined catalyst precursor to obtain the cobalt-manganese oxide catalyst composition (see Colley (1988) Ind. Eng. Chem. Res. 27:1339-1344). It was found that the catalyst precursor comprised the mixed spinels $Co_2MnO_4$ and $Co_2Mn_2O_4$. Reduction of the catalyst precursor resulted in an unsupported catalyst composition comprising metallic Co, MnO and a certain amount of mixed spinels $Co_2MnO_4$ and $Co_2Mn_2O_4$.

It was the disadvantage of the prior art that F-T synthesis of hydrocarbon products result in a mixture of undesired products and less desired olefin products. A major drawback of conventional unsupported cobalt-manganese oxide F-T catalysts is their relatively low activity resulting in a relatively low syngas conversion rate.

It was an object of the present invention to provide an improved Fischer-Tropsch catalyst (F-T catalyst) having superior catalyst activity while maintaining high hydrocarbon selectivity and low carbon dioxide ($CO_2$) and methane ($CH_4$) selectivity. In another aspect, it was an object of the present invention to provide an improved process for producing a higher yield of ethylene and propylene from syngas in addition to value added products, such as 1-hexene and 1-butene.

SUMMARY

The present invention relates to a catalyst composition comprising cobalt manganese oxide which is modified with silica in the form of a hydrophilic silica, the catalyst further comprises at least one of lanthanum, phosphorus, Fe, Zr and Zn and optionally one or more basic elements selected from the group consisting of alkali metal, alkaline earth metal and transition metal. Furthermore, a method for preparing said catalyst composition and a process for producing aliphatic and aromatic hydrocarbons using said catalyst composition is provided.

DETAILED DESCRIPTION

Compositions

Figure 1:
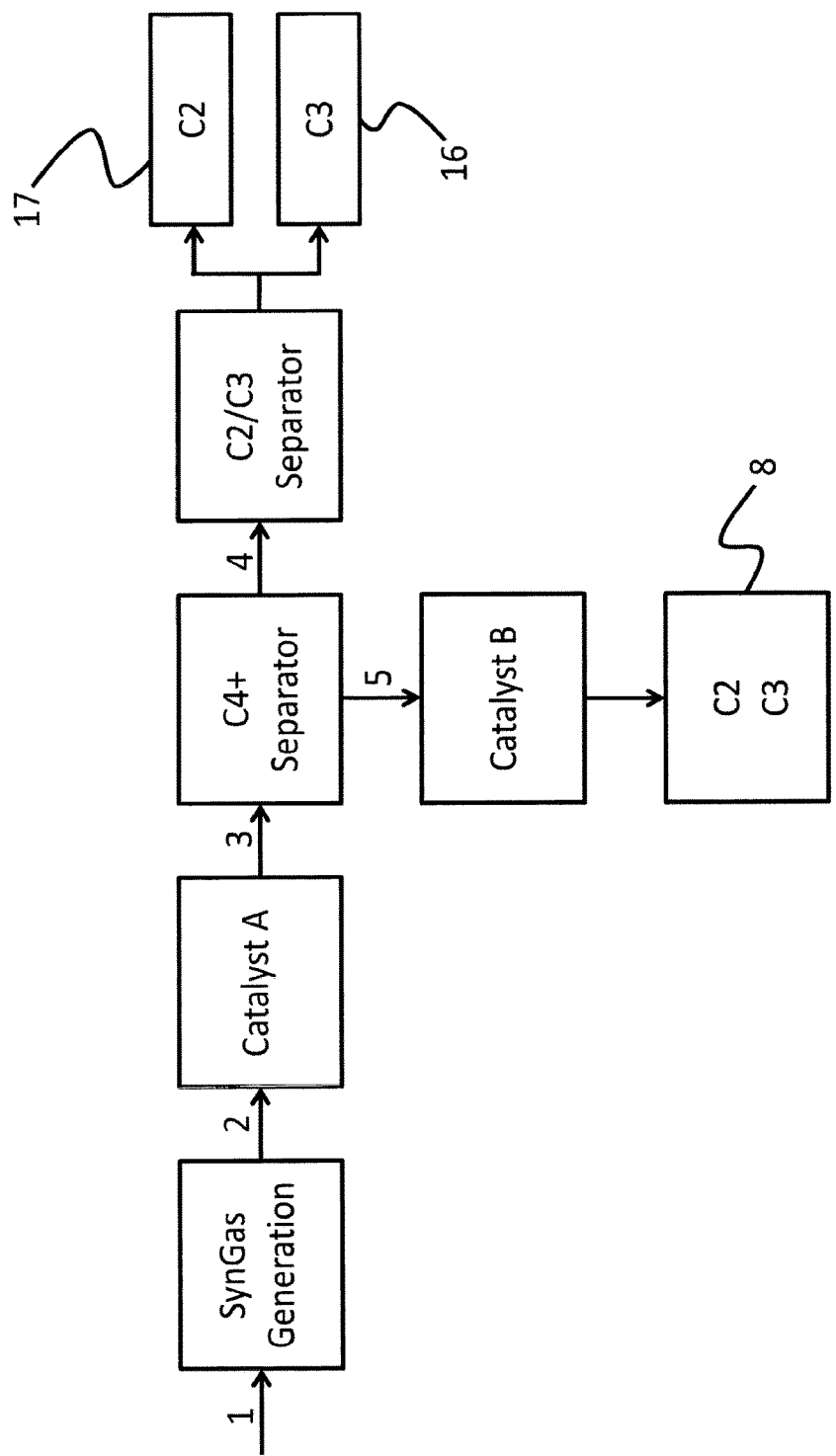
FIG. 1 shows a scheme of an embodiment of the process according to the present invention.

The solution to the above problem is achieved by providing the embodiments as described herein below and as characterized in the claims. Accordingly, the present invention provides a catalyst composition comprising cobalt; manganese; a hydrophilic silica; and at least one element selected from the group of lanthanum, phosphorus, Fe, Zr and Zn, wherein the relative molar ratios of the elements comprised in said composition are represented by the formula

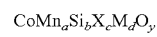

$CoMn_aSi_bX_cM_dO_y$, wherein:
M is one or more elements selected from the group consisting of alkali metal, alkaline earth metal and transition metal;
a is from about 0.8 to about 1.2;
b is from about 0.1 to about 1;
each c is from greater than 0 to about 0.005, wherein the total c is from greater than 0 to about 0.005;
d is from about 0 to about 0.005;
X is at least one element selected from the group consisting of lanthanum, phosphorus, Fe, Zr and Zn;
y is a number determined by the valence of the other elements present; and
Si is in the form of a hydrophilic silica.

In the context of the present invention, it was surprisingly found that the catalyst activity of a conventional cobalt manganese oxide FT-catalyst can be significantly increased when said conventional catalyst is modified with a hydrophilic silica, such as, for example, an AEROSIL® hydrophilic silica from Evonik, and at least one element selected from the group consisting of lanthanum, phosphorus, Fe, Zr and Zn and optionally one or more elements selected from the group consisting of alkali metal, alkaline earth metal and transition metal. Furthermore, it was found that the catalyst of the present invention has a decreased selectivity for $CO_2$ and $CH_4$ which are unwanted side products of F-T synthesis. Hence, the catalyst provided by the present invention is particularly suitable for converting a syngas mixture into a hydrocarbon comprising product stream. In one aspect, the hydrocarbon is an olefin.

The molar ratio of Co:Mn is about 1:0.8-1.2 (depicted as: $CoMn_a$ wherein a is 0.8-1.2). This means that the molar ratio of Co:Mn is between about 1:0.8: and about 1:1.2. In another aspect, the molar ratio of Co:Mn is about 1:0.9-1.1. In yet another aspect, the molar ratio of Co:Mn is about 1:1. The molar ratio of Co:Mn can be important to obtain a catalyst composition having a high light olefin selectivity and a low methane selectivity. The relative ratio of cobalt and manganese has a strong effect on selectivity of the catalyst for hydrocarbons. When the Co:Mo ratio is too high, the hydrogenation activity of the catalyst is increased leading to an increased methane selectivity.

The catalyst composition of the present invention comprises silicon in the form of a hydrophilic silica (depicted as: $Si_b$ wherein b is 0.1 to 1). The subscript 'b' is intended to refer to the molar ratio of the Si relative to Co. Thus, for example, Co:$Si_b$ is 1:0.1 to 1. In one aspect, $Si_b$ is 0.1, 0.2, 0.3, 0.4, 0.5, 0.6, 0.7, 0.8, 0.9 or 1.0. In one aspect, the hydrophilic silica can have a pH of from about 3.7 to about 4.7, for example, about 3.7, 3.8, 3.9, 4, 4.1, 4.2, 4.3, 4.4, 4.5, 4.6, or 4.7. In another aspect, the hydrophilic silica can have a pH less than about 3.7 or greater than about 4.7 and the present invention is not intended to be limited to a hydrophilic silica having any particular pH value. In another aspect, the hydrophilic silica has a specific surface area of from about 200 $m^2/g$ to about 400 $m^2/g$, for example, about 200, 225, 250, 275, 300, 325, 350, 375, or 400 $m^2/g$. Similarly, in other aspects, the hydrophilic silica can have a specific surface area less than about 200 $m^2/g$ or greater than about 400 $m^2/g$ and the present invention is not intended to be limited to a hydrophilic silica having any particular specific surface area. In one aspect, the hydrophilic silica is a pyrogenic silica, having a low bulk density and produced from a flame based process. In another aspect, the hydrophilic silica can comprise an AEROSIL® silica, available from Evonik Industries.

The catalyst composition of the present invention also comprises at least one element selected from the group consisting of lanthanum, phosphorus, Fe, Zr and Zn (depicted as $X_c$ wherein each c is from greater than 0 to about 0.005, wherein the total c is from greater than 0 to about 0.005). In one aspect, the catalyst composition comprises one element. If the catalyst composition comprises one element, the element can be selected from the group consisting of Fe, Zr, and Zn. In another aspect, the catalyst composition comprises two elements. If the catalyst composition comprises two elements, the elements can be lanthanum and phosphorus. In one embodiment, accordingly, the catalyst comprises lanthanum but does not comprise phosphorus. In one embodiment, the catalyst comprises phosphorus but does not comprise lanthanum. In yet another embodiment, the catalyst comprises both lanthanum and phosphorus. For example, if the catalyst composition comprises both lanthanum and phosphorus, then c for each lanthanum and phosphorus is from greater than 0 to about 0.005, wherein the total c is from greater than 0 to about 0.005. Thus, when X is more than one element, for example two elements, the value of c for the first element added to the value of c for the second element has a value of from greater than 0 to about 0.005. In one aspect, the molar ratio of Co:X is at least 1: about $10^{-6}$ in case the catalyst composition comprises lanthanum; at least 1: about $10^{-5}$; or at least 1: about $5 \times 10^{-5}$. In one aspect, the molar ratio of Co:P is at least 1: about $10^{-6}$ in case the catalyst composition comprises phosphorus; at least 1: about $10^{-5}$; or at least 1: about $5 \times 10^{-5}$. c refers to the molar ratio of the Si relative to X. Thus, for example, Co:$X_c$ is greater than 0 to about 0.005. The term "greater than 0" means that said element can be present in the catalyst composition.

The catalyst composition of the present invention further can comprise one or more additional elements selected from the group consisting of alkali metal element, alkaline earth metal element and transition metal element (depicted herein as "M"). In the context of the present invention, it was found that $CO_2$ formation and the therewith associated coke deposition by the Boudouard reaction can be suppressed when the catalyst composition further comprises one or more basic elements selected from the group consisting of alkali metal elements, alkaline earth metal elements and transition metal elements. As used herein, the term "basic element" relates to an element that forms a "Lewis base" (i.e. an element that is able to provide a pair of electrons and thus capable of coordination to a Lewis acid, thereby producing a Lewis adduct) and/or a "Brønsted base" (i.e. an element capable of accepting a proton from a acid or the corresponding chemical species) in the catalyst composition.

In one aspect, the one or more alkali metals that can be in the catalyst composition are selected from the group consisting of sodium (Na), potassium (K), rubidium (Rb) and caesium (Cs). In another aspect, the one or more alkali metals are selected from the group consisting of sodium (Na), potassium (K) and caesium (Cs). In yet another aspect, the one or more alkali metals is potassium (K). The one or more alkaline earth metals that can be in the catalyst composition can be selected from the group consisting of magnesium (Mg), calcium (Ca), strontium (Sr) and barium (Ba); or selected from the group consisting of magnesium (Mg) and calcium (Ca). The one or more transition metal elements that can be in the catalyst composition of the present invention can be selected from "Group 4 of the Periodic Table" or from the group consisting of titanium (Ti) and zirconium (Zr).

The amount of alkali metal, alkaline earth metal and/or transition metal elements ("M") that can be in the catalyst composition of the present invention is determined by the molar ratio in relation to the cobalt present in the catalyst composition. In case the catalyst composition comprises M, the molar ratio Co:M is up to 1: about 0.005 (1: about $5 \times 10^{-3}$; also depicted as: $CoM_d$ wherein d is from greater than 0 to about 0.005), or up to 1: about $10^{-3}$. In another aspect, the molar ratio of Co:M is at least 1: about $10^{-6}$ in case the catalyst composition comprises M; at least 1: about $10^{-5}$; or at least 1: about $5 \times 10^{-5}$. d can also be 0, meaning that M is absent.

In this respect, it should be noted that the catalyst of the present invention is a mixed oxide catalyst and not a catalyst wherein the active elements are deposited on a catalyst support. The unsupported catalyst of the present invention is fundamentally different than F-T catalysts wherein Co and Mn are deposited on a (metal) oxide catalyst support. Nevertheless, the catalyst composition can further comprise a (metal) oxide, e.g. as a binder or a diluent.

Accordingly, the catalyst composition of the present invention can further comprise a binder (support or substrate) which can be selected from the group consisting of magnesia, alumina, silica, zirconia, titania, activated carbon, non-activated carbon, or zeolites. The zeolite, if present, can be a mesoporous zeolite or a microporous zeolite. In one aspect, the binder can be fluidized. In another aspect, the binder can be a shaped form.

The catalyst composition can have at least a lower methane formation, a lower carbon dioxide formation, a higher activity, a higher activity, a higher conversion of syngas, or a higher total olefins formation as compared to a the same catalyst without the $Si_b$ component. Thus, for example, a catalyst composition comprising $Si_b$, lanthanum and phosphorus can have a higher total olefin formation than a catalyst composition without the $Si_b$ component but with the lanthanum and phosphorus. In another example, a catalyst composition comprising $Si_b$, lanthanum and phosphorus can covert more CO in syngas that a catalyst composition without the $Si_b$ component but with the lanthanum and phosphorus.

Methods

Also disclosed herein, is a method of producing olefins comprising contacting syngas with the catalyst compositions described herein.

Also disclosed herein, is a method of making a catalyst composition as described herein.

In a further embodiment, the present invention relates to a method for preparing the catalyst composition as described herein, wherein said method comprises the steps:
(a) preparing a solution of cobalt- and manganese-comprising salts to form a cobalt-manganese-solution;
(b) admixing an alkaline solution to the cobalt-manganese-solution to form a precipitate;
(c) admixing a hydrophilic silica and a solution of at least one lanthanum, phosphorus, Fe, Zr and Zn salt; such as, for example, a solution of a salt comprising one or more elements selected from the group consisting of alkali metal elements, alkaline earth metal elements and transition metal elements to the solution comprising the precipitate of Co and Mn formed in step (b to form a modified precipitate;
(d) separating the modified precipitate from the liquid, washing and drying the modified precipitate to form a dried precipitate;
(e) calcining the dried precipitate in air to form a calcined catalyst precursor; and
(f) contacting the calcined catalyst precursor with a reducing agent.

Suitable reducing agents include, but are not limited to, CO and $H_2$.

In another aspect, the method for preparing the catalyst composition of the invention comprises the steps (a)-(f) in the herein above described order.

In the cobalt-manganese-solution preparation step (a) as described herein, a solution comprising soluble cobalt- and manganese-comprising salts is prepared. The solvent and the obtained solution can be heated to facilitate dissolving of the cobalt- and manganese-comprising salts. In another aspect, the solvent and the obtained solution is heated to at least about 60° C. and up to about 95° C. (about 60-95° C.), or to about 80° C.

In the present method for preparing the catalyst composition, the solution can be made in any suitable solvent. Suitable solvents are all compounds in which the chosen salts are soluble and which are easy to remove again in the separation step as defined herein. In one aspect, an aqueous solution can be used. In a specific aspect, the solvent is water ($H_2O$).

In the precipitate forming step (b) as described herein, a precipitate is formed by converting the soluble cobalt- and manganese-comprising salts into insoluble compounds by admixing an alkaline solution, for example, under constant agitation. In one aspect, the precipitate is formed by admixing a suitable amount of ammonium hydroxide and/or sodium carbonate solution, such as, for example, ammonium hydroxide solution, to a cobalt-manganese-solution. The amount of alkaline compound present in the alkaline solution is selected so that it is at least sufficient for the stoichiometric reaction with the soluble cobalt- and manganese-comprising salts present. In another aspect, the amount of alkaline compound present in the alkaline solution is 1-10 times the stoichiometric amount. In yet another aspect, the ammonium hydroxide and/or sodium carbonate solution is heated to the same temperature as the cobalt-manganese-solution. The temperature of the mixture can be kept constant until the precipitate is formed under constant agitation.

In the modified precipitate forming step (c) as described herein, a solution of a hydrophilic silica is admixed with a solution containing at least one of a lanthanum, phosphorus, Fe, Zr, and Zn salt, such as a lanthanum-comprising salt; and/or a solution of a phosphorus-comprising salt; such as, for example, a solution of a salt comprising one or more elements selected from the group consisting of the alkali metal elements, the alkaline earth metal elements and the transition metal elements is admixed to the solution comprising the Co/Mn precipitate formed in step (b) of the method, for example, under continuous agitation, to form a modified precipitate. The solution of a salt comprising one or more elements selected from the group consisting of the alkali metal elements, the alkaline earth metal elements and the transition metal elements can be added at the same time or after adding the solution of a lanthanum-comprising salt; and/or a solution of a phosphorus-comprising salt. In another aspect, the solution of a salt comprising one or more elements selected from the group consisting of the alkali metal elements, the alkaline earth metal elements and the transition metal elements is added after adding the solution of a lanthanum-comprising salt; and/or a solution of a phosphorus-comprising salt. The solutions used in the modified precipitate forming step can be made in any suitable solvent. In one aspect, aqueous solutions can be used. In a specific aspect, the solvent can be is water ($H_2O$).

In the precipitate separation step (d) as described herein, the modified precipitate (i.e. the solid phase of the mixture that is formed after completing the modified precipitate forming step (c)) is separated from the liquid (i.e. the liquid phase of the mixture that is formed after completing the modified precipitate forming step (c)) using any conventional method which allows the separation of a precipitate from a solvent. Suitable methods include, but are not limited to, filtering, decanting and centrifugation. Subsequently the obtained precipitate is washed using the solvent in which the solutions were made, for example, with water or distilled water. The modified precipitate is then dried, for example, at about 110-120° C. for about 4-16 hours to form a dried precipitate.

In the calcining step (e) as described herein, the dried precipitate is calcined in air to form a calcined catalyst precursor. In one aspect, the dried precipitate is calcined at about 500-600° C. for about 4-24 hours. The calcined but unreduced catalyst mainly comprises the spinel $Co_2MnO_4$.

After calcination, the calcined catalyst precursor can be formed into pellets using any conventional method. Said pellets can subsequently be sieved to obtain regularly sized particles. Said particles can be sized between about 0.65-0.85 mm.

In the reducing step (f) as described herein, the calcined catalyst precursor is contacted with a reducing agent. This is to partially reduce the comprised Co to its metallic state and results in the formation of cobalt manganese oxide comprising catalyst as defined herein. In addition thereto, the catalyst composition comprises metallic Co supported on MnO at the end of the reducing step. Hence, the MnO is not reduced completely into metallic Mn. Accordingly, the catalyst composition of the present invention, inter alia comprising metallic cobalt, MnO and mixed spinels having the formula $Co_2MnO_4$ and $Co_2Mn_2O_2$, is obtainable by the herein described method for preparing a catalyst composition after the "reducing step" is finished. Suitable reducing agents include, but are not limited to, CO and $H_2$.

Accordingly, the reducing step is very important for the method for preparing a catalyst composition of the present invention. When the reducing step is performed too mild, an insufficient amount of Co is reduced to its metallic state. When the reducing step is performed too harsh, the catalyst composition comprises an insufficient amount of "cobalt manganese oxide" and/or MnO. The skilled person can easily determine that the catalyst obtained catalyst composition comprises metallic cobalt, MnO and cobalt manganese oxide by using standard analytical techniques, including X-ray diffraction.

Any suitable reducing agent can be used in the reducing step of this invention. In one aspect, the reducing step is performed using a reducing agent in the gas phase. In one aspect, the reducing agent can be selected from the group consisting of hydrogen ($H_2$) and carbon monoxide (CO). The reduction can be carried out at ambient temperature or at elevated temperature. In one aspect, the reduction is carried out at a temperature of at least about 300° C.; at least about 350° C. and up to about 500° C.; or up to about 450° C. In one aspect, calcined catalyst precursor is contacted with a reducing agent for at least about 14 hrs; at least about 16 hrs and up to about 24 hrs; or up to about 20 hrs.

In another aspect, the reducing step is performed "in situ". The term "in situ" is well known in the field of chemical engineering and refers to industrial plant operations or procedures that are performed in place. For example, aged catalysts in industrial reactors can be regenerated in place (in situ) without being removed from the reactors; see e.g. WO 03/041860 and WO 03/076074. In the context of the present invention, accordingly, a catalyst composition that is reduced in situ refers to a catalyst composition wherein the reducing step is performed in place, i.e. in the same enclosure that is later present in the process installation in which the catalysed process takes place. In one embodiment, the reducing step as defined herein is performed while the "calcined catalyst precursor" is already present in the catalyst enclosure that is situated in the process installation wherein the catalyst composition is to be employed. In a further embodiment, the reducing step as defined herein is performed while the "calcined catalyst precursor" is already present in the catalyst enclosure which can be directly placed into said process installation.

In a further embodiment of the present invention a catalyst composition obtainable by the herein above described method for preparing a catalyst composition is provided. Accordingly, the present invention relates to a catalyst composition obtainable by the method comprising the steps:
(a) preparing a solution of cobalt- and manganese-comprising salts to form a cobalt-manganese-solution;
(b) admixing to the cobalt-manganese-solution to form a precipitate by addition of alkaline solution;
(c) admixing a hydrophilic silica and a solution of a at least one lanthanum, phosphorus, Fe, Zr and Zn sal, such as a solution of a lanthanum-comprising salt; and/or a solution of a phosphorus-comprising salt, such as, for example, a solution of a salt comprising one or more elements selected from the group consisting of alkali metal elements, alkaline earth metal elements and transition metal elements so as to form a solid that can be evaporated and dried, and then added to the solution comprising the precipitate of Co and Mn formed in step (b) to form a modified precipitate;
(d) separating the modified precipitate from the liquid, washing and drying the modified precipitate to form a dried precipitate;
(e) calcining the dried precipitate in air to form a calcined catalyst precursor; and
(f) contacting the calcined catalyst precursor with a reducing and passivation agent.

In a further embodiment, the present invention relates to a process for producing a product stream comprising a mixture of aliphatic and aromatic hydrocarbons comprising contacting the catalyst composition as described herein with a gaseous mixture comprising hydrogen and carbon monoxide (syngas mixture). In one aspect, the product stream comprising a mixture of aliphatic and aromatic hydrocarbons can be produced by Fischer-Tropsch synthesis.

The terms "aliphatic hydrocarbons" and "aromatic hydrocarbons" are very well known in the art. Accordingly, an "aliphatic hydrocarbons" relates to acyclic or cyclic, saturated or unsaturated hydrocarbon compounds that are not aromatic hydrocarbons. The term "aromatic hydrocarbons" relates to cyclically conjugated hydrocarbons with a stability (due to delocalization) that is significantly greater than that of a hypothetical localized structure (e.g. Kekulé structure). The most common method for determining aromaticity of a given hydrocarbon is the observation of diatropicity in the $^1$H NMR spectrum.

In the context of the present invention, it was surprisingly found that substantially no waxes are produced in the process for Fischer-Tropsch synthesis of the present invention. Moreover, it was found that the selectivity for lower hydrocarbons having between 2 and 5 carbon atoms (C2-C5 HC) and aromatic hydrocarbons is increased.

In the process of the present invention, the catalyst composition can be, in one aspect, comprised in a fixed bed reactor or a fluidized bed reactor.

In another aspect, the syngas mixture has a hydrogen ($H_2$) to carbon monoxide (CO) molar ratio of about 1-4 (i.e. $H_2$: CO is 1: about 1-4). The term "syngas mixture" as used herein relates to a gaseous mixture comprising substantially hydrogen ($H_2$) and carbon monoxide (CO). The syngas mixture, which is used as a feed stream to the present process for producing aliphatic and aromatic hydrocarbons, can comprise up to 10 mol-% of other components such as $CO_2$ and lower hydrocarbons (lower HC). Said other components can be side-products or unconverted products obtained in the process used for producing the syngas mixture. In another aspect, the syngas mixture comprises substantially no molecular oxygen ($O_2$). As used herein, the term "syngas mixture comprising substantially no $O_2$" relates to a syngas mixture which comprises such a low amount of $O_2$ so that the comprised $O_2$ does not interfere with the Fischer-Tropsch synthesis reaction. In another aspect, the syngas mixture comprises not more than 1 mol-% $O_2$; not more than 0.5 mol-% $O_2$; or not more than 0.4 mol-% $O_2$.

The process conditions useful in the process of the present invention can be easily determined by the person skilled in the art; see Dry (2004) Stud. Surf. Sci. Catal 152:197-230 in "Fischer-Tropsch technology" eds. Steynberg and Dry. Accordingly, the Fischer-Tropsch synthesis is performed at a reaction temperature of about 150-350° C., a space velocity of about 400-5000 $h^{-1}$, for example, about 2000 $h^{-1}$ and a pressure of between atmospheric and about 5 MPa. The catalyst can be stabilized for about 80-100 hours at about 150-350° C. before actual use.

In this respect, it should be noted that the reaction conditions have a marked effect on the catalytic performance. It has been reported that selectivity on a carbon basis is essentially a function of the probability of chain growth, α; see Dry (2004) loc. cit. Control of the product selectivity is to a large extent determined by the factors that influence the value of α. The main factors are the temperature of the reaction, the gas composition and more specifically the partial pressures of the various gases in contact with catalyst inside the reactor. Overall, by manipulating these factors a high degree of flexibility can be obtained regarding the type of product and the carbon range. An increase in FT-synthesis operating temperature shifts the selectivity profile to lower carbon number products. Desorption of growing surface species is one of the main chain termination steps and since desorption is an endothermic process so a higher temperature should increase the rate of desorption which will result in a shift to lower molecular mass products. Similarly, the higher the CO partial pressure the more is the catalyst surface covered by adsorbed monomers. The lower the coverage by partially hydrogenated CO monomers the higher the probability of chain growth is expected to be; see also Mirzaei et al., Adv. Phys. Chem., 2009, 1-12. Accordingly, the two key steps leading to chain termination are desorption of the chains yielding alkenes and hydrogenation of the chains to yield alkanes.

In a further embodiment, the present invention relates to a process for producing a product stream comprising a mixture of aliphatic and aromatic hydrocarbons comprising the method for preparing the catalyst composition as described herein and contacting the obtained catalyst composition with a syngas mixture.

In the present invention, the product stream comprising a mixture of aliphatic and aromatic hydrocarbons can, in one aspect, be produced by Fischer-Tropsch synthesis.

Accordingly, the present invention provides a process for producing a product stream comprising a mixture of aliphatic and aromatic hydrocarbons, for example, by Fischer-Tropsch synthesis, comprising:
(a) preparing a solution of cobalt- and manganese-comprising salts to form a heated cobalt-manganese-solution;
(b) admixing ammonium hydroxide or sodium carbonate solution to the cobalt-manganese-solution to form a precipitate;
(c) admixing a hydrophilic silica and a solution of a at least one lanthanum, phosphorus, Fe, Zr and Zn sal, such as a solution of a lanthanum-comprising salt; and/or a solution of a phosphorus-comprising salt; such as, for example, a solution of a salt comprising one or more elements selected from the group consisting of alkali metal elements, alkaline earth metal elements and transition metal elements to the solution comprising the precipitate of Co and Mn formed in step (b) to form a modified precipitate;
(d) separating the modified precipitate from the liquid, washing and drying the modified precipitate to form a dried precipitate;
(e) calcining the dried precipitate in air to form a calcined catalyst precursor;
(f) contacting the calcined catalyst precursor with a reducing agent to produce a catalyst composition; and
(g) contacting the obtained catalyst composition with a syngas mixture.

In other aspects, the present invention provides methods for utilizing the catalyst systems described herein for the production of desirable F-T hydrocarbon products. In the various embodiments described below, with respect to F-T processes, the first catalyst composition can comprise the promoting elements dispersed hydrophilic silica containing the catalyst composition described above.

Integrated Process

In the process according to the present invention, the syngas is first contacted with a first catalyst composition to be converted to a first product stream, for example, by Fischer-Tropsch synthesis. The first product stream comprises ethylene, propylene and aliphatic hydrocarbons having 4 or more carbon atoms. The first product stream can further comprise other components such as methane, ethane, propane, aromatic hydrocarbons and $CO_2$.

In one aspect, the aliphatic hydrocarbons having 4 or more carbon atoms comprises aliphatic hydrocarbons having 4-10 carbon atoms; 4-8 carbon atoms; or 4-6 carbon atoms.

In one aspect, the aliphatic hydrocarbons having 4 or more carbon atoms essentially consist of aliphatic hydrocarbons having 4-10 carbon atoms; 4-8 carbon atoms; or 4-6 carbon atoms. The term "essentially consist of" in this context can mean at least 95 wt %, at least 99 wt % or at least 99.5 wt %.

The aliphatic hydrocarbons having 4 or more carbon atoms can comprise e.g. butane, butene, pentane, pentene, hexane and hexene. The aliphatic hydrocarbons having 4 or more carbon atoms can, in one aspect, comprise 1-butene and 1-hexene.

The first product stream is split into two product streams: a product stream of aliphatic hydrocarbons having 4 or more carbon atoms and a product stream of aliphatic hydrocarbons having 3 or less carbon atoms. This step can be done by a depropanizer, which is well-known to the skilled person.

The first product stream is split into a second product stream comprising at least 90 wt % of said aliphatic hydrocarbons having 4 or more carbon atoms and a third product stream comprising ethylene and propylene. The second product stream can, in one aspect, comprise at least 95 wt %, at least 99 wt %; or at least 99.5 wt % of said aliphatic hydrocarbons having 4 or more carbon atoms. The remainder of the second product stream is the component of the first product stream. In another aspect, the third product stream comprises aliphatic hydrocarbons having 4 or more carbon atoms.

The third product stream comprises no or little amount of aliphatic hydrocarbons having 4 or more carbon atoms. The third product stream can, in one aspect, comprise at most 10 wt %; at most 5 wt %; or at most 1 wt % or more, for example at most 0.5 wt % of the aliphatic hydrocarbons having 4 or more carbon atoms. In another aspect, the third product stream does not comprise the aliphatic hydrocarbons having 4 or more carbon atoms.

The third product stream comprises ethylene and propylene. In the cases where the third product stream comprises other components, said other components can, in one aspect, be other aliphatic hydrocarbons having 3 or less carbon atoms such as methane, ethane and propane. In another aspect, the third product stream comprises at least 90 wt %; at least 95 wt %; at least 99 wt %; or at least 99.5 wt % of aliphatic hydrocarbons having 3 or less carbon atoms.

In another aspect, a large portion of the third product stream is ethylene and propylene. In other aspects, the third product stream comprises at least 30 wt %; at least 50 wt %; at least 75 wt %; or at least 90 wt % of ethylene and propylene.

Ethylene and propylene are separated from the third product stream so as to form a first ethylene stream and a first propylene stream.

Further, the second product stream is converted into a fourth product stream comprising ethylene and/or propylene. The fourth product stream can be split into a second ethylene stream and a second propylene stream. The first and second ethylene and/or the first and second propylene stream can be combined.

The process according to the present invention has an advantage that ethylene and propylene are obtained in two ways. Ethylene and propylene are directly obtained from the syngas by a conversion using the first catalyst composition. Furthermore, the aliphatic hydrocarbons having 4 or more carbon atoms from the first product stream is converted to ethylene and/or propylene. Hence, the process according to the present invention results in an overall high yield of ethylene and/or propylene.

In one aspect, the fourth product stream comprising ethylene and/or propylene is mixed with the first product stream. This can be done by feeding said fourth product stream back to the unit for splitting the first product stream into the second and the third product streams, e.g. depropanizer. During the conversion of the second product stream, aromatics can also be produced, mainly benzene, toluene and xylene. Before the fourth product stream is mixed with the first product stream, these aromatics can, in one aspect, be separated from the fourth product stream.

The first product stream can further comprise methane, ethane and propane. In this case, methane, ethane and propane in the first product stream can be included in the third product stream by the splitting step of the first product stream. In this case, step c) can comprise the steps of:

c1) removing methane from the third product stream to obtain a fifth product stream comprising ethane, ethylene, propane and propylene, c2) separating the fifth product stream into a sixth product stream comprising ethane and ethylene and a seventh product stream comprising propane and propylene, c3) removing ethane from the sixth product stream to form the first ethylene stream and c3') removing propane from the seventh product stream to form the first propylene stream, In step c1), methane is removed from the third product stream. The remaining product stream, i.e. the fifth product stream comprises ethane, ethylene, propane and propylene and, in one aspect, comprises low amount of methane. The fifth product stream can comprise at most 10 wt %, at most 5 wt %, at most 1 wt % or at most 0.5 wt % of methane. The fifth product stream can comprise at least 90 wt %, at least 95 wt %, at least 99 wt %, or at least 99.5 wt % of ethane, ethylene, propane and propylene. This step can be done by a demethanizer, which is well-known to the skilled person.

Subsequently, the fifth product stream is separated into a six product stream comprising ethane and ethylene and a fifth product stream comprising propane and propylene in step c2). This can be done by a deethanizer, which is well-known to the skilled person. The sixth product stream can comprise at least 90 wt %, at least 95 wt %, at least 99 wt %, at least 99.5 wt % of ethane and ethylene. The seventh product stream can comprise at least 90 wt %, at least 95 wt %, at least 99 wt %, or at least 99.5 wt % of propane and propylene.

Subsequently, the sixth product stream is separated into ethane and ethylene e.g. by a C2 splitter and the seventh product stream is separated into propane and propylene e.g. by a C3 splitter.

In one aspect, propane removed from the seventh product stream in step c3') is dehydrogenated into propylene and mixed with the seventh product stream. The propylene obtained can be fed back to the C3 splitter. This results in an even higher overall yield of propylene. Suitable ways for dehydrogenation of propane into propylene is well-known to the skilled person.

In another aspect, methane removed from the third product stream of step c1) is added to the syngas. This stream comprising methane can be collected from the demethanizer into a recycle unit and fed from the recycle unit to the syngas generation unit for feeding the syngas. Similarly, in one aspect, ethane removed from the sixth product stream in step c3) can be added to the syngas. Ethane can be collected from the C2 splitter into a recycle unit and fed from the recycle unit to the syngas generation unit for feeding the syngas. The recycle unit for collecting methane and ethane can be the same unit and can mix methane and ethane before feeding the mixture gas to the syngas generation unit.

The terms "aliphatic hydrocarbons" and "aromatic hydrocarbons" are very well known in the art. Accordingly, an "aliphatic hydrocarbons" relates to acyclic or cyclic, saturated or unsaturated hydrocarbon compounds that are not aromatic hydrocarbons. The term "aromatic hydrocarbons" relates to cyclically conjugated hydrocarbons with a stability (due to delocalization) that is significantly greater than that of a hypothetical localized structure (e.g. Kekulé structure). The most common method for determining aromaticity of a given hydrocarbon is the observation of diatropicity in the $^1$H NMR spectrum.

In the context of the present invention, it was surprisingly found that substantially no waxes are produced in the process for Fischer-Tropsch synthesis of the present invention. Moreover, it was found that the selectivity for lower hydrocarbons having between 2 and 5 carbon atoms (C2-C5 HC) and aromatic hydrocarbons is increased.

In the process of the present invention, the first catalyst composition can, in one aspect, be in a fixed bed reactor or a fluidized bed reactor.

In a further embodiment, the present invention relates to the process for producing ethylene and propylene as described above comprising the method for preparing the first catalyst composition as described herein.

In one aspect of the present invention, the first product stream can be produced by Fischer-Tropsch synthesis.

Second Catalyst Composition

According to the process of the present invention, the second product stream is converted into a fourth product stream comprising ethylene and/or propylene. In one aspect, this can be performed by contacting the second product stream with a second catalyst composition suitable for converting aliphatic hydrocarbons having 4 or more carbon atoms into ethylene and/or propylene. In one aspect, the second catalyst composition is an olefin metathesis catalyst or $C_4$ to $C_8$ cracking catalyst suitable for converting 1-butylene and 1-hexene into ethylene and propylene.

Suitable examples for the second catalyst composition include an olefin metathesis catalyst. Examples of suitable catalysts are described e.g. in U.S. Pat. No. 6,586,649, which is incorporated herein by reference in terms of the catalyst:

The second catalyst composition can be at least one metal oxide selected from the group consisting of the oxides of the transition metals.

In one aspect, the transition metal oxide catalyst in the second catalyst composition can be selected from oxides of molybdenum, or of rhenium or of tungsten, or of mixtures of any two or more of tungsten, rhenium and molybdenum.

This catalyst can be a homogeneous (unsupported) catalyst or a heterogeneous (supported) catalyst. In another aspect, the catalyst can be supported and any convenient support can be used, provided it neither interferes with nor inhibits the metathesis step of the process according to the invention. Suitable supports include those based on or including ceramic supports such as silica, alumina, titania, zirconia or mixtures thereof. In a specific aspect, a suitable support can be silica. The catalyst can be attached to its support in any convenient fashion, such as those known in the art, in particular by sublimation or by wet impregnation. The transition metal oxide constituent of the catalyst can amounts to 1-30% by mass of the total catalyst mass (transition metal and support together), for example, 6-20% thereof. In particular the catalyst can be a $WO_3$-based (tungsten oxide-based) catalyst containing Cs (caesium) as a promoter.

In the cases where the second catalyst composition is a supported catalyst type, the transition metal oxide can form e.g. 1-30% by mass of the total heterogeneous catalyst mass. In particular, the catalyst of the heterogeneous catalyst mass can comprise tungsten oxide, being supported on silica, the catalyst mass containing a promoter selected from the group consisting of cesium (to decrease selectivity towards propylene) and phosphates (to increase selectivity towards propylene).

In one aspect, the second catalyst composition has as high a proportion of acid sites thereon as practicable. Acidity of the catalyst can be enhanced by treating the catalyst with organic acids or inorganic acids, or by impregnation thereof with cations such as those of phosphates or borates. Acidity of the catalyst can, conversely, be reduced by blocking acid sites thereon, by means of alkaline earth metals.

Many other suitable olefin metathesis catalysts are known, for example as described in U.S. Pat. Nos. 8,153,851 and 5,990,369.

The present invention will now be more fully described by the following non-limiting Examples and figures.

In FIG. 1, feedstock 1 such as natural gas, coal, biomass or municipal solid waste is fed to the syngas generation unit. The syngas generated 2 is contacted with a first catalyst composition (catalyst A) to obtain a first product stream 3 comprising ethylene and propylene and aliphatic hydrocarbons having 4 or more carbon atoms. The first product stream 3 is fed to a C4+ separator to split the first product stream 3 into a second product stream 5 comprising at least 90 wt % of said aliphatic hydrocarbons having 4 or more carbon atoms and a third product stream 4 comprising ethylene and propylene.

The third product stream 4 is fed to a C2/C3 separator to separate ethylene and propylene in the third product stream 4. A first ethylene stream 17 and a first propylene stream 16 are obtained.

The second product stream 5 is contacted with a second catalyst composition (catalyst B) so that a fourth product stream 8 comprising ethylene and/or propylene is produced.

Figure 2:
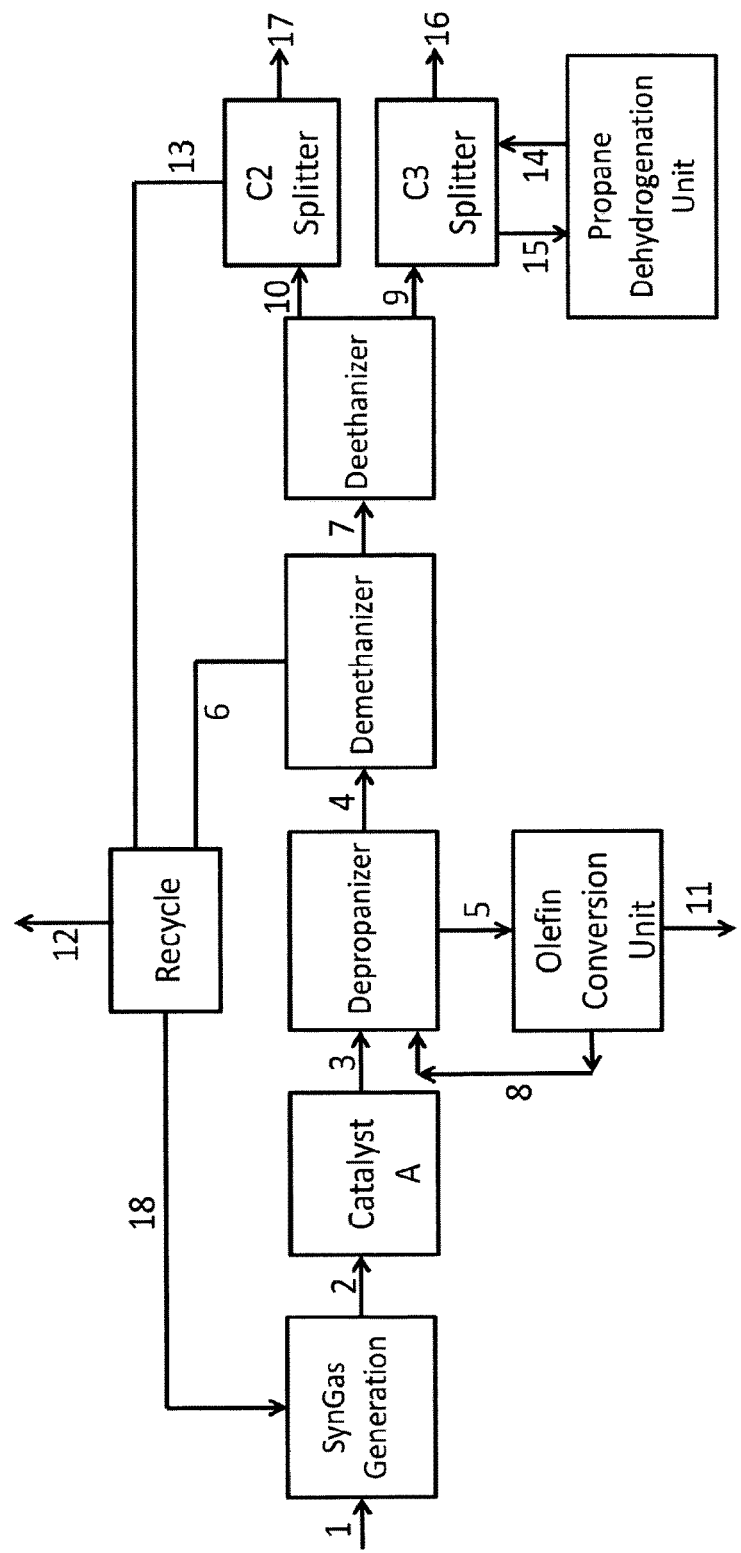
FIG. 2 shows a further embodiment of the process according to the present invention.

FIG. 2 shows a further embodiment of the process according to the present invention. Feedstock 1 is fed to the syngas generation unit which produces syngas 2. The syngas 2 is contacted with the first catalyst composition (catalyst A) to obtain a first product stream 3. The first product stream 3 is fed to the depropanizer to split the first product stream 3 into a second product stream 5 comprising at least 90 wt % of the aliphatic hydrocarbons having 4 or more carbon atoms and a third product stream 4 comprising ethylene and propylene.

The second product stream 5 is contacted with a second catalyst composition in the olefin conversion unit, which produces a fourth product stream 8 comprising ethylene and propylene and a product stream 11 comprising BTX. The fourth product stream 8 is fed back to the depropanizer and is mixed with the first product stream 3.

The third product stream 4 is fed to the demethanizer and methane 6 is removed from the third product stream 4, producing a fifth product stream 7 which comprises ethane, ethylene, propane and propylene. Methane 6 is fed to the recycle unit, which removes undesired components 12 and feeds the remainder 18 to the syngas generation unit.

The fifth product stream 7 is fed to the deethanizer and is separated into a sixth product stream 10 comprising ethane and ethylene and a seventh product stream 9 comprising propane and propylene.

The sixth product stream 10 is fed to the C2 splitter, which separates ethane 13 and ethylene 17. Ethane 13 is fed to the recycle unit, which removes undesired compounds 12 and feeds the remainder 18 to the syngas generation unit.

The seventh product stream 9 is fed to the C3 splitter, which separates propane 15 and propylene 16. Propane 15 is fed to the propane dehydrogenation unit, which dehydrogenates propane into propylene 14. Propylene 14 is fed back to the C3 splitter.

EXAMPLE 1 (Comparative)

CoMnLaP (Comprising 0.1 wt-% La and 0.03 wt-% P)

100 ml of Co and Mn (1 M solutions) were premixed and heated to 80° C. in a round bottom flask. Ammonium hydroxide solution (5.6 M/l) preheated at 80° C. was added to the nitrate solution, which was continuously stirred whilst the temperature was maintained at 80° C. The pH was varied from 2.80 to 8.0. The desired quantity of lanthanum nitrate (0.0117 g) was dissolved in 3.4 ml of distilled water and was added slowly into the of CoMn catalyst precipitate (5 g) followed by addition of 0.0064 g of ammonium phosphate dissolved in 3.4 ml of distilled water. The resulting precipitate was mixed thoroughly to make a homogeneous mixture. Material was dried at 110° C. for 16 h-24 h and calcined at 500-600° C. for 24 h. The calcined catalyst precursor was pelleted and sieved to obtain 0.65-0.85 mm sized particles. Calcined precursor particles (0.5 g) were loaded into a fixed-bed reactor and tested at standard conditions.

EXAMPLE 2

CoMnP (Comprising 0.05 wt-% P)

100 ml of Co and Mn (1 M solutions) were premixed and heated to 80° C. in a round bottom flask. Ammonium hydroxide solution (5.6 M/l) preheated at 80° C. was added to the nitrate solution, which was continuously stirred whilst the temperature was maintained at 800° C. The pH was varied from 2.80 to 8.0. the desired quantity of ammonium phosphate (0.0107 g) dissolved in 3.4 ml of distilled water was added slowly into the of CoMn catalyst precipitate (5 g). The resulting precipitate was mixed thoroughly to make a homogeneous mixture. Material was dried at 110° C. for 16 h-24 h and calcined at 500-600° C. for 24 h. The calcined catalyst precursor was pelleted and sieved to obtain 0.65-0.85 mm sized particles. Calcined precursor particles (0.5 g) were loaded into a fixed-bed reactor and tested at standard.

EXAMPLE 3

CoMnSiLaP 100 ml of Co and Mn (1 M solutions) were premixed and heated to 80-90° C. in a round bottom flask. 1.2 g of hydrophilic silica having a pH ofr from about 3.7 to about 4.7 and a specific surface area of 200 m²/g to 400 m²/g, 0.005 g of lanthanum nitrate, and 0.005 g of ammonium phosphate were dissolved in 20-50 ml of water under continues agitation for 1-2 hrs at temperature where water does not evaporate. The resulting mixture was dried by the incipient wetness method. Resultant solid was added to Co/Mn solution. Sodium carbonate 1 M solution preheated at 60 to 80° C. was added to this Co/Mn solution, which was continuously stirred whilst the temperature was maintained at 80° C. The pH was varied from 2.80 to 9 by addition of carbonate solution. Resulting precipitate were aged for ½ to 8 hr followed by separating of precipitate from the liquid. The resulting precipitate were washed till sodium free. Material was dried at 110-120° C. for 16 h-24 h and cooked at 300-500° C. for 4-24 h followed by passivation of catalyst precursor with an appropriate media and thermal treatment. The catalyst precursor was pelleted and sieved to obtain 40-60 mesh sized particles. Catalyst particles (0.5 g) were loaded into a fixed-bed reactor and tested at standard conditions.

EXAMPLE 4

CoMnSiLaP 100 ml of Co and Mn (1 M solutions) were premixed and heated to 80-90° C. in a round bottom flask. 1.2 g of hydrophilic silica having a pH of from about 3.7 to about 4.7 and a specific surface area of 200 m²/g to 400 m²/g; 0.01 g of lanthanum nitrate, and 0.01 g of ammonium phosphate were dissolved in 20-50 ml of water under continues agitation for 1-2 hrs at temperature where water does not evaporate. The resulting mixture was dried by the incipient wetness method. Resultant solid was added to Co/Mn solution. Sodium carbonate 1 M solution preheated at 60 to 80° C. was added to this Co/Mn solution, which was continuously stirred whilst the temperature was maintained at 80° C. The pH was varied from 2.80 to 9 by addition of carbonate solution. Resulting precipitate were aged for ½ to 8 hr followed by separating of precipitate from the liquid. The resulting precipitate were washed till sodium free. Material was dried at 110-120° C. for 16 h-24 h and cooked at 300-500° C. for 4-24 h followed by passivation of catalyst precursor with an appropriate media and thermal treatment. The catalyst precursor was pelleted and sieved to obtain 40-60 mesh sized particles. Catalyst particles (0.5 g) were loaded into a fixed-bed reactor and tested at standard conditions.

EXAMPLE 5

CoMnSiLaP 100 ml of Co and Mn (1 M solutions) were premixed and heated to 80-90° C. in a round bottom flask. 1.2 g of hydrophilic silica having a pH of from about 3.7 to about 4.7 and a specific surface area of 200 m²/g to 400 m²/g, 0.031 g of lanthanum nitrate and 0.01 g of ammonium phosphate were dissolved in 20-50 ml of water under continues agitation for 1-2 hrs at temperature where water does not evaporate. The resulting mixture was dried by the incipient wetness method. Resultant solid was added to Co/Mn solution. Sodium carbonate 1 M solution preheated at 60 to 80° C. was added to this Co/Mn solution, which was continuously stirred whilst the temperature was maintained at 80° C. The pH was varied from 2.80 to 9 by addition of carbonate solution. Resulting precipitate were aged for ½ to 8 hr followed by separating of precipitate from the liquid. The resulting precipitate were washed till sodium free. Material was dried at 110-120° C. for 16 h-24 h and cooked at 300-500° C. for 4-24 h followed by passivation of catalyst precursor with an appropriate media and thermal treatment. The catalyst precursor was pelleted and sieved to obtain 40-60 mesh sized particles. Catalyst particles (0.5 g) were loaded into a fixed-bed reactor and tested at standard conditions.

EXAMPLE 6

CoMnZnSi 100 ml of Co and Mn (1 M solutions) were premixed and heated to 80-90° C. in a round bottom flask. 1.2 g of hydrophilic silica having a pH of from about 3.7 to about 4.7 and a specific surface area of 200 m²/g to 400 m²/g, and 2.98 g of Zinc nitrate were dissolved in 20-50 ml of water under continues agitation for 1-2 hrs at temperature where water does not evaporate. The resulting mixture was dried by the incipient wetness method. Resultant solid was added to Co/Mn solution. Sodium carbonate 1 M solution preheated at 60 to 80° C. was added to this Co/Mn solution, which was continuously stirred whilst the temperature was maintained at 80° C. The pH was varied from 2.80 to 9 by addition of carbonate solution. Resulting precipitate were aged for ½ to 8 hr followed by separating of precipitate from the liquid. The resulting precipitate were washed till sodium free. Material was dried at 110-120° C. for 16 h-24 h and cooked at 300-500° C. for 4-24 h followed by passivation of catalyst precursor with an appropriate media and thermal treatment. The catalyst precursor was pelleted and sieved to obtain 40-60 mesh sized particles. Catalyst particles (0.5 g) were loaded into a fixed-bed reactor and tested at standard conditions.

EXAMPLE 7

CoMnFeSi 100 ml of Co and Mn (1 M solutions) were premixed and heated to 80-90° C. in a round bottom flask. 1.2 g of hydrophilic silica having a pH of from about 3.7 to about 4.7 and a specific surface area of 200 m²/g to 400 m²/g, and 3.62 g of iron nitrate were dissolved in 20-50 ml of water under continues agitation for 1-2 hrs at temperature where water does not evaporate. The resulting mixture was dried by the incipient wetness method. Resultant solid was added to Co/Mn solution. Sodium carbonate 1 M solution preheated at 60 to 80° C. was added to this Co/Mn solution, which was continuously stirred whilst the temperature was maintained at 80° C. The pH was varied from 2.80 to 9 by addition of carbonate solution. Resulting precipitate were aged for ½ to 8 hr followed by separating of precipitate from the liquid. The resulting precipitate were washed till sodium free. Material was dried at 110-120° C. for 16 h-24 h and cooked at 300-500° C. for 4-24 h followed by passivation of catalyst precursor with an appropriate media and thermal treatment. The catalyst precursor was pelleted and sieved to obtain 40-60 mesh sized particles. Catalyst particles (0.5 g) were loaded into a fixed-bed reactor and tested at standard conditions.

TABLE 1

CATALYST ACTIVITY

| Catalyst | EXAMPLE | | | | | | |
|---|---|---|---|---|---|---|---|
| | 1 CoMnLaP | 2 CoMnP | 3 CoMnSiLaP | 4 CoMnSiLaP | 5 CoMnSiLaP | 6 CoMnSiZn | 7 CoMnSiFe |
| Conversion % | 42.4 | 21.7 | 83.8 | 58.5 | 60.2 | 76 | 81 |
| Methane | 13.1 | 14.2 | 4.7 | 11.7 | 13 | 29.5 | 31.5 |
| Paraffin | 25.2 | 21.4 | 18.3 | 19.7 | 20.5 | 20 | 21.5 |
| Total Olefins | 55.4 | 56.4 | 67.5 | 60.3 | 56 | 20.4 | 33.5 |
| $CO_2$ | 6.3 | 8 | 14.2 | 8.3 | 10.5 | 30.1 | 13.5 |

Table 1 shows that the catalyst of the present invention has a significantly increased activity when compared to a catalyst without the $Si_b$ component. Table 1 show that the catalyst of the present invention, which includes the $Si_b$ component has a significantly increased activity when compared to a other and conventional cobalt manganese oxide F-T catalyst. For example, the catalysts in Examples, 3, 4, and 5 shows increased conversion rates and increased production in olefins. In addition thereto, the catalysts form Examples 3, 4, and 5, shows a decrease methane formation, which is an undesired side-product produced in F-T synthesis.

EXAMPLE 8

Ethylene and propylene were produced from syngas according to the scheme as illustrated in FIG. 2.

A catalyst composition as described herein can be used as the first catalyst composition (catalyst A), i.e. the first catalyst composition used is unsupported and comprises cobalt; manganese; and at least one element selected from the group of lanthanum and phosphorus, wherein the relative molar ratios of the elements comprised in said composition are represented by the formula

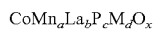
$CoMn_aLa_bP_cM_dO_x$ wherein:

M is one or more elements selected from the group consisting of alkali metal, alkaline earth metal and transition metal;

a is about 0.8-1.2;

b and/or c is from greater than 0 to about 0.005;

d is from 0 to about 0.005; and x is a number determined by the valence of the other elements present.

It should be noted that the first catalyst composition can also comprise a hydrophilic silica containing catalyst, as described herein. The obtained first product stream had a composition as shown in Table 2.

The aliphatic hydrocarbons having 4 or more carbon atoms (indicated as C4+) was fed to an olefin conversion unit. The obtained product stream contained a major amount of ethylene and propylene and a minor amount of BTX, as can be seen in Table 1.

Hence, the total amount of the obtained ethylene and propylene significantly increased by the conversion of C4+ into ethylene and propylene compared to the case in which only the first catalyst composition was used.

TABLE 2

| | Syngas Feed Kg/hr | First product stream Kg/hr | Feed to olefin conversion unit Kg/hr | Products of olefin conversion unit Kg/hr | Total Kg > hr | % Increase |
|---|---|---|---|---|---|---|
| Ar | | | | | | |
| CO | 206938 | 16063 | | | | |
| H2 | 41870 | 23892 | | | | |
| N2 | 560 | 560 | | | | |
| CO2 | | 5149 | | | | |
| C2 | | 2571 | | | | |
| C2= | | 16994 | | 12024 | 29018 | |
| C3 | | 2231 | | | | |
| C3= | | 25492 | | 18041 | 43533 | |
| C4+ | | 37570 | 37570 | | | |
| BTX | | | | 340 | | |
| total | | 130522 | 37570 | 30065 | | |
| Total C2 C3 olefins | | 42486 | | | 72551 | 70.8 |

EXAMPLE 9

In this example, propane obtained by C3 splitter was fed to a propane dehydrogenation unit. This resulted in an even higher amount of propylene in the final product, as shown in Table 3.

TABLE 3

| | Syngas Feed Kg/hr | First product stream Kg/hr | Feed To olefin conversion unit Kg/hr | Products of olefin conversion unit Kg/hr | Feed to PDH | PDH Product | Total Kg/hr | % Increase |
|---|---|---|---|---|---|---|---|---|
| Ar | | | | | | | | |
| CO | 206938 | 16063 | | | | | | |
| H2 | 41870 | 23892 | | | | | | |
| N2 | 560 | 560 | | | | | | |
| CO2 | | 5149 | | | | | | |
| C2 | | 2571 | | | | | | |
| C2= | | 16994 | | 12024 | | | 29018 | |
| C3 | | 2231 | | | 2231 | | | |
| C3= | | 25492 | | 18041 | | 2130 | 45663 | |
| C4+ | | 37570 | 37570 | | | | | |
| BTX | | | | 340 | | | | |
| total | | 130522 | 37570 | 30065 | | | | |
| Total C2 C3 olefins | | 42486 | | | | | 74681 | 75.8 |

The invention claimed is:

1. A catalyst composition comprising cobalt; manganese; hydrophilic silica; and at least one element selected from the group consisting of lanthanum, phosphorus, Fe, Zr, and Zn, wherein the relative molar ratios of the elements comprised in the composition are represented by the formula $$CoMn_aSi_bXcM_dO_y$$

wherein:
M is one or more elements selected from the group consisting of alkali metal, alkaline earth metal, and transition metal;
a is about 0.8-1.2;
b is 0.1 to 1;
each c is from greater than 0 to about 0.005, wherein the total c is from greater than 0 to about 0.005;
d is 0 to about 0.005;
X is at least one element selected from the group consisting of lanthanum, phosphorus, Fe, Zr, and Zn;
y is a number determined by the valence of the other elements present; and
$Si_b$ is present as part of the catalyst composition.

2. The catalyst according to claim 1, wherein M is selected from the group consisting of sodium (Na), potassium (K), rubidium (Rb), caesium (Cs), magnesium (Mg), calcium (Ca), strontium (Sr), barium (Ba), titanium (Ti), and zirconium (Zr).

3. The catalyst composition according to claim 1, wherein X is two elements, wherein the elements are lanthanum and phosphorus, and wherein c for each of lanthanum and phosphorus is from greater than 0 to about 0.005.

4. The catalyst composition according to claim 1, wherein the hydrophilic silica has a pH of 3.7-4.7.

5. The catalyst composition according to claim 1, wherein the hydrophilic silica has a specific surface area of 200 m²/g to 400 m²/g.

6. The catalyst composition according to claim 1, wherein X is one element and wherein the element is selected from the group consisting of Fe, Zr, and Zn.

7. The catalyst composition according to claim 1, wherein the catalyst has at least one of lower methane formation, lower carbon dioxide formation, higher activity, higher conversion of syngas, or higher total olefins formation as compared to the same catalyst without the $Si_b$ component.

8. The catalyst composition of claim 1, wherein the hydrophilic silica comprises a pyrogenic silica.

9. A method for preparing the catalyst composition of claim 1, comprising the steps:
(a) preparing a solution of cobalt- and manganese-comprising salts to form a cobalt-manganese-solution;
(b) admixing an alkaline solution to the cobalt-manganese-solution to form a precipitate;
(c) admixing a hydrophilic silica and a solution of at least one of a lanthanum, phosphorus, Fe, Zr, and Zn salt; and/or a solution of a phosphorus-comprising salt; evaporating any water present therein and drying, and then adding the resulting solid to the solution comprising the precipitate to form a modified precipitate;
(d) separating the modified precipitate, washing and drying the modified precipitate to form a dried precipitate;
(e) calcining the dried precipitate in air to form a calcined catalyst precursor; and
(f) contacting the calcined catalyst precursor with a reducing agent.

10. The method according to claim 9, wherein the reducing agent is selected from the group consisting of hydrogen ($H_2$) and carbon monoxide (CO).

11. The process according to claim 9, wherein the process comprises admixing a solution of a lanthanum-comprising salt; and/or a solution of a phosphorus- comprising salt.

12. A method of producing olefins comprising contacting syngas with the catalyst composition of claim 1.

13. A process for producing a product stream comprising a mixture of aliphatic and aromatic hydrocarbons, the process comprising contacting the catalyst composition of claim 1 with a syngas mixture.

14. The process according to claim 13, wherein the product stream comprises a mixture of aliphatic and aromatic hydrocarbons produced by Fischer-Tropsch synthesis.

15. The process according to claim 13, wherein the catalyst composition is in a fixed bed reactor or fluidized bed reactor.

* * * * *